United States Patent [19]
Tsuji et al.

[11] 4,420,564
[45] Dec. 13, 1983

[54] BLOOD SUGAR ANALYZER HAVING FIXED ENZYME MEMBRANE SENSOR

[75] Inventors: Nobuhiko Tsuji; Keijiroh Nakamura, both of Yokosuka; Koichi Endoh, Hino; Toshiyoshi Hamada; Keiichi Ishida, both of Tokyo, all of Japan

[73] Assignee: Fuji Electric Company, Ltd., Kawasaki, Japan

[21] Appl. No.: 318,000

[22] Filed: Nov. 4, 1981

[30] Foreign Application Priority Data

| Nov. 21, 1980 | [JP] | Japan | 55-163334 |
| Nov. 21, 1980 | [JP] | Japan | 55-163335 |
| Dec. 9, 1980 | [JP] | Japan | 55-172658 |
| Dec. 9, 1980 | [JP] | Japan | 55-172659 |
| Dec. 9, 1980 | [JP] | Japan | 55-172661 |
| Dec. 9, 1980 | [JP] | Japan | 55-172662 |
| Dec. 9, 1980 | [JP] | Japan | 55-172663 |

[51] Int. Cl.$^3$ .................................. G01N 33/66
[52] U.S. Cl. .................................. 435/288; 204/403; 204/415; 364/415; 364/416; 422/81; 435/14; 435/291; 435/817; 436/95; 436/150
[58] Field of Search ............... 422/81; 435/288, 291, 435/817; 204/195 B, 1 T; 364/415, 416, 497

[56] References Cited

U.S. PATENT DOCUMENTS

| 3,542,662 | 11/1970 | Hicks | 435/190 X |
| 3,770,607 | 11/1973 | Williams | 204/195 B X |
| 3,902,970 | 9/1975 | Levin | 204/195 B X |
| 3,920,969 | 11/1975 | Berglas | 204/195 B X |
| 3,960,497 | 6/1976 | Acord | 364/415 X |
| 4,224,405 | 9/1980 | Hijikata | 435/288 X |

Primary Examiner—Sidney Marantz
Attorney, Agent, or Firm—Brumbaugh, Graves, Donohue & Raymond

[57] ABSTRACT

A blood sugar analyzing apparatus has a reaction cell which houses a fixed enzyme membrane sensor and a measuring electrode which receives a blood specimen which causes a chemical reaction between the blood specimen and said fixed enzyme membrane for measuring the blood sugar concentration in the specimen on the basis of a reaction current signal generated in the sensor by the chemical reaction. The analyzing apparatus has a microcomputer for calculating a conversion coefficient used for converting the reaction current into a blood sugar concentration value by introducing a standard solution having a known blood sugar concentration, for storing data representing the value of said conversion coefficient, for calculating a blood sugar concentration value of a test specimen based upon the stored conversion coefficient value and reaction current from the test specimen. A display and printer provide a read-out of the blood sugar concentration value obtained. The microcomputer controls temperature and timing of the measurement process, as well as other control functions.

15 Claims, 22 Drawing Figures

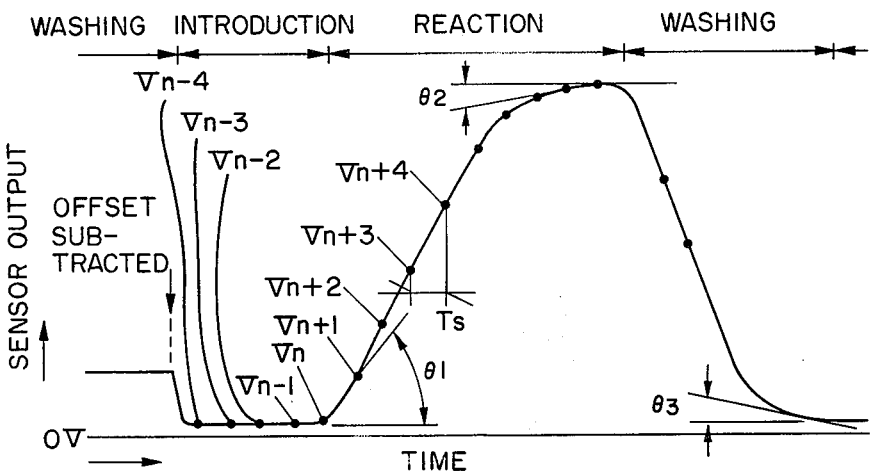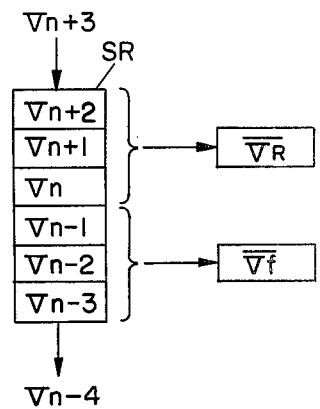
FIG. 7a  FIG. 7b
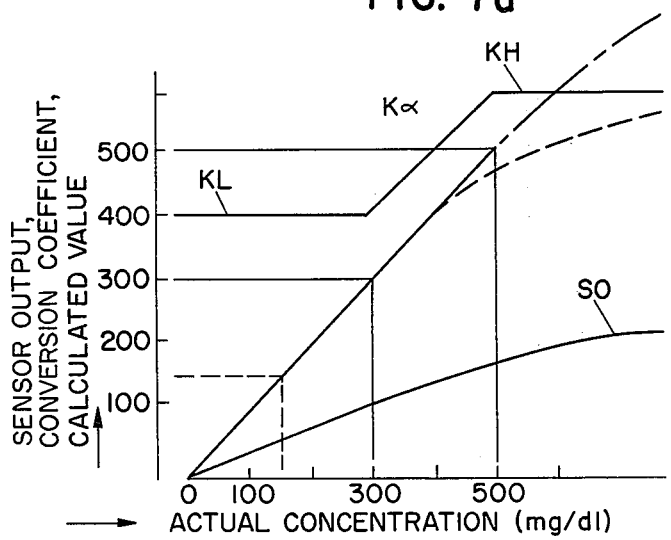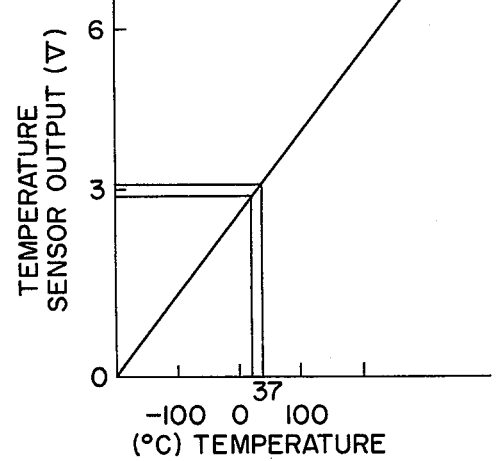
FIG. 8  FIG. 9
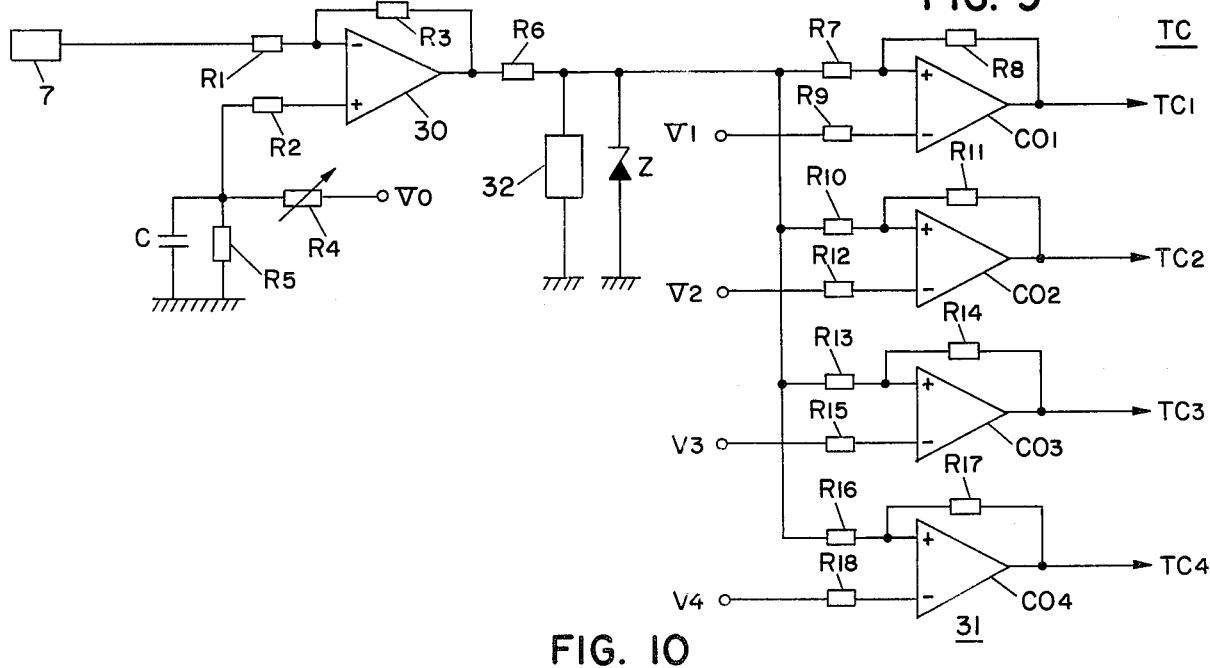
FIG. 10

BLOOD SUGAR ANALYZER HAVING FIXED ENZYME MEMBRANE SENSOR

BACKGROUND OF THE INVENTION

1. Field of the Invention

The present invention relates to a total-bloodtype blood sugar analyzer for use in hospitals, clinics, and analyzer companies for analyzing the concentration of glucose or blood sugar in a blood specimen (total blood, blood serum, or blood plasma of a human being or animal) in a short period of time using a small amount of blood sample.

2. Description of the Prior Art

Blood sugar analyzers of the type described above measure a sugar content or glucose concentration by supplying a blood specimen or standard solution (hereinafter referred to as blood specimen or the like) with a blood sugar content to a fixed enzyme membrane (glucose oxidase membrane) to cause a chemical reaction therebetween, which generates a reaction current in proportion to the blood sugar contained in the blood. The blood sugar analyzers comprise a fixed enzyme membrane electrode (composed of an electrode surface of platinum and silver to which a membrane of blood sugar oxidase is intimately attached), and a reaction cell which houses the electrode and receives a blood specimen or the like. Since the chemical reaction is generally susceptible to temperatures, the blood sugar analyzers include a temperature sensor for detecting temperatures in the reaction cell to maintain the reaction cell and adjacent areas at a predetermined temperature under the control of an output from the temperature sensor.

FIG. 1 illustrates a conventional glucose analyzer, and FIG. 2 is a graph showing the output from a blood sugar sensor plotted against a measuring operation sequence of the analyzer.

An output from the blood sugar or glucose sensor in the analyzer is converted into a blood sugar or glucose concentration (in units of mg/dl) and displayed on a display 12. A conversion coefficient can be obtained by measuring a standard solution having a known blood sugar or glucose concentration which is introduced into an analyzer body 11 through an inlet port 14. It has been conventional practice in obtaining such a conversion coefficient to turn an adjustment knob 13 until a displayed value on the display 12 is brought into conformity with the known blood sugar concentration in the standard solution. However, such an adjustment is tedious and time-consuming, and a variable resistor actuatable by the knob 13 is required to be of a high precision, adding to the cost of the analyzer.

Obtaining a correct measurement requires that an offset portion (which corresponds to a base portion appearing as the output of the blood sugar sensor before a blood specimen or the like is introduced for measurement, and which is indicated by OFF in FIG. 2) be removed from the output of the blood sugar sensor. For such removal of the offset portion, it has been customary to establish a suitable threshold value TH in advance, to compare a sensor output SO with the threshold value TH, to regard a chemical reaction as being started when the sensor output SO becomes larger than the threshold value, and then to subtract the offset portion from the sensor output SO from that time on, thus reaching a net quantity involved in the reaction. However, the prior practice is disadvantageous in that, where the threshold value is too high, a blood sample with a low blood sugar concentration cannot be measured, and conversely, where the threshold value is too low, noises or variations in the base portion are included in measurements. The offset portion cannot correctly be defined for its value, and hence measurement results have not been accurate.

An enzyme membrane sensor used heretofore has suffered the drawback that it does not provide linearity in a range of higher concentrations, that is, the proportional relationship between measured values and actual concentrations is not assured in such a higher concentration range, resulting in a tendency to produce errors in measurement in a wide range of concentrations.

Also, the results of blood sugar concentration measurement have been handwritten, and hence wrong values are liable to be recorded in error.

The analyzer according to the prior art effects measurements by going through various modes of operation, as shown in FIG. 2, including introduction of a blood specimen or the like, allowing a chemical reaction to take place, washing away of the blood specimen or the like which has gone through the chemical reaction, and introduction of a next blood specimen or the like. The modes of operation are repeated for a number of measurements. Such modes of operation are divided by predetermined intervals of time, which are monitored to effect shifting from one mode to a next mode of operation. With such time-governed control, a transition may not be carried out even when the condition for such transition has already occurred, or a transition may be effected too early with the result that sufficient measurement may not be performed. Therefore, the analyzer has suffered a lowered capability of handling specimens or is prone to incorrect measurements. When the time interval for washing the reaction cell is too long, the analyzer has a lowered handling capability and is wasteful of a buffer liquid. Accordingly, a more efficient control system for controlling the time of washing would be desirable.

SUMMARY OF THE INVENTION

It is an object of the present invention to eliminate the problems of the prior devices described above by providing a digital processing device which automatically effects decisions defined above and wherein a printer is provided for printing information about diagnosis and maintenance.

The above object can be achieved by the blood sugar analyzer according to the present invention which has a reaction cell which houses a fixed enzyme membrane and a measuring electrode and which receives a blood specimen to cause a chemical reaction between the blood specimen and said fixed enzyme membrane for measuring the blood sugar concentration in the blood specimen based upon a reaction current generated in said measuring electrode by the chemical reaction. The invention provides means for computing a conversion coefficient used for converting said reaction current into the glucose concentration, means for correcting the conversion coefficient according to a measured blood sugar concentration, means for monitoring the conditions of parts of the analyzer and the way in which the chemical reaction progresses on the basis of said reaction current and the temperature in the reaction cell, and means for ascertaining whether information derived from such monitoring meets predetermined measurement conditions. Also, means for controlling the parts of the analyzer are provided as well as means for printing or displaying the processed results from the processor.

Numerous other advantages and features of the present invention will become readily apparent from the following detailed description of the invention and embodiments thereof, from the claims and from the accompanying drawings.

BRIEF DESCRIPTION OF THE DRAWINGS

Embodiments of the present invention will be described with reference to the drawings in which:

FIGS. 7a and 7b are a set of diagrams showing transient conditions in a sequence of measuring operations;

FIG. 8 is a graph illustrative of the way in which a conversion coefficient is corrected;

FIG. 9 is a graph showing output characteristics of a temperature sensor;

FIG. 10 is a block diagram of a temperature detecting system according to another embodiment of the invention;

DETAILED DESCRIPTION OF THE PREFERRED EMBODIMENTS

Figure 1:
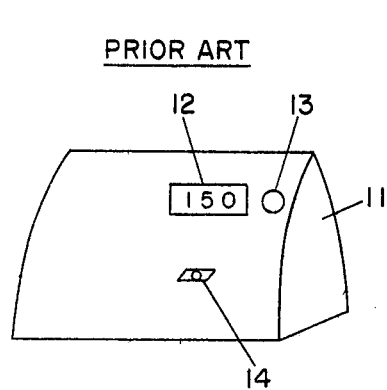
FIG. 1 is a view showing an appearance of a conventional analyzer.
Figure 2:
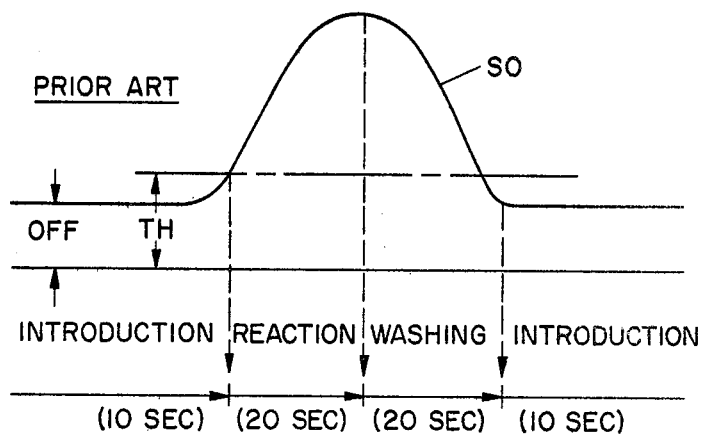
FIG. 2 is a graph indicative of an output of a glucose sensor as plotted against a sequence of measuring operations of the analyzer.

While this invention is susceptible of embodiment in many different forms, there is shown in the drawings and will herein be described in detail one specific embodiment, and alternatives thereof with the understanding that the present disclosure is to be considered an an exemplification of the principles of the invention and is not intended to limit the invention to the embodiment illustrated.

In the drawing figures, a blood sugar measurement electrode or sensor 1 for measuring a reaction current proportional to a blood sugar concentration comprises an electrode of platinum and silver having on its surface a membrane of blood sugar oxidase attached thereto. The blood sugar measurement electrode 1 and a temperature electrode 2 are disposed in a reaction cell CE. A buffer liquid 4 is delivered by a liquid pump 3 into the cell CE wherein the liquid 4 washes the interior of the cell CE. After a reaction has been finished, the buffer liquid 4 is discharged as a drainage liquid 5. An air pump 6 vibrates a silicon diaphragm SD to stir a blood specimen or the like which has been introduced through an inlet port OP into the cell CE, thereby uniformizing the concentration of the blood specimen in the cell CE. A temperature sensor 7 detects the temperature of the cell block. A heater 8 heats the cell block up to a temperature of the human or animal body from which the sample was taken (for example, 37° C. for a human). Thus, the blood in the cell CE is maintained at a temperature equal to the temperature of a human body, if samples from humans are being tested.

A control device CC comprised mainly of a microcomputer CPU is connected to a blood sugar analyzing unit BSU through lines $L_1$ through $L_6$. The control device CC reads out a reaction current from the measurement electrode 1 over the line $L_1$, reads out an amount of temperature compensation with respect to a measured value over the line $L_2$, measures and controls the temperature of the cell block SB over the lines $L_4$, $L_5$, and controls operation of liquid pump 3 and air pump 6 over the lines $L_3$, $L_6$, respectively. The control device CC is also connected to various switches $MO_1$ through $MO_4$, $DS_1$, $DS_2$, a display unit DI, and a printer P through lines $L_7$ through $L_{11}$ for controlling input and output devices and the overall operation of the analyzer. Designated at $DS_1$ is a specimen number setting switch, at $DS_2$ is a standard solution value setting switch, at CAL and RUN are mode displays for indicating calibration and operation modes, respectively, and at $MO_1$ through $MO_4$ are mode setting switches for setting the foregoing modes and a paper feed mode for the printer P, and for setting the switch $DS_1$.

In the control device (FIG. 5) of the present invention, the blood sugar measuring electrode or blood sugar sensor 1 produces an output, which is amplified by a differential amplifier 21, the output of which is converted by an A/D converter 22 into a digital quantity. An output from the A/D converter 22 is fed via a buffer 23 to a microcomputer CPU in which the input signal is digitally processed so as to be converted into a corresponding blood sugar concentration (mg/dl), which is displayed. A latch 26, a digital-to-analog (D/A) converter 25, and a buffer amplifier 24 serve to measure an offset portion appearing as an output of the blood sugar sensor 1 before a blood specimen or the like is introduced into the analyzer and aid in removal of the measured offset portion from the output of the sensor 1.

An output from a temperature sensor 7 is amplified by a buffer amplifier 27, the output of which is converted into a temperature code by a temperature comparator or encoder 28 comprising an A/D converter, a comparator and other suitable elements. The coded signal is then delivered through a buffer 29 to the microcomputer CPU which determines the degree of the temperature in the blood sugar analyzing unit BSU on the basis of the output from the temperature comparator 28, and which is responsive to the result of such determination for turning on or off a heater 8 in the blood sugar analyzing unit for temperature control of the latter.

In normal measurements, when a blood specimen or the like is introduced through the inlet port OP into the reaction cell CE, a chemical reaction takes place between the blood sugar in the blood specimen or the like and the fixed enzyme membrane, causing a reaction current to flow in the blood sugar sensor as described above. When the chemical reaction is in equilibrium (regarded as termination of the chemical reaction), the value of the reaction current is converted into a corresponding value of blood sugar concentration for the blood specimen or the like being tested. Such conversion is effected by converting the value of the reaction current into a corresponding voltage value, which is then multiplied by a conversion coefficient that has previously been given upon measurement of a standard solution. The measured concentration value is displayed on the display DI of the seven-segment type and at the same time printed out by the printer P. Information as to various parts of the analyzer which are related to measurements and information as to the reaction process are all delivered to the control device CC in which the supplied information is processed for control of the analyzer.

The foregoing operation is performed when the parts of the blood sugar analyzer meet predetermined measuring conditions and the chemical reaction progresses normally. When the control device CC diagnoses the blood sugar analyzer as falling in one of the following conditions, an error code corresponding to the diagnosed condition is indicated on the display DI and printed out by the printer P.

The conditions are enumerated below and will be described with reference to FIGS. 4 and 5.

1. The cell CE does not reach a predetermined temperature capable of measurements. As described above, the blood sugar analyzer is easily affected by temperatures, and to cope with the problem, the reaction cell CE is required to be maintained at a constant temperature.

2. The temperature of the reaction cell CE exceeds a range of temperatures capable of measurements.

3. The offset portion is greater than a predetermined value because the measuring electrode or blood sugar electrode 1 is unstable.

4. The offset portion varies, and varies to a large degree before a blood specimen or the like is put into the reaction cell CE.

5. The blood sugar sensor 1 has a reduced degree of reaction sensitivity.

6. The blood sugar sensor 1 has an increased degree of reaction sensitivity.

7. The fixed enzyme membrane sensor has deteriorated and has a slow response.

8. Measured values exceed the measurable range.

9. A measurement is made without calibration of the analyzer. The calibration is necessary to obtain a conversion coefficient by measuring a standard solution prior to measurement of the blood sugar concentration in a blood specimen or the like.

10. Two or more out of the conditions 1 through 9 are met.

The conditions 1 and 2 can be easily diagnosed by converting an output from the temperature sensor 7 into a temperature code as described above with reference to FIG. 5 and by comparing such temperature code with a predetermined set value. Error codes for these conditions may be indicated as EO1, EO2, for example.

The conditions 3 through 8 are diagnosed on the basis of an output from the blood sugar sensor 1.

More specifically, the conditions 3 and 4 can be diagnosed by comparing an output issued from the differential amplifier 21 prior to introduction of the blood specimen or the like, that is, by comparing an offset portion with a predetermined value, or by sampling the offset portion and comparing a present value with a past value thereof. Error codes for these conditions may be EO3, EO4, for example.

The conditions 5 and 6 are met when the output from the blood sugar sensor 1 is respectively smaller and larger than a predetermined value. In order for the condition 5 to be established, the output from the blood sugar sensor 1 is small enough to render calibration impossible, and in order for the condition 6 to be met, the output from the blood sugar sensor 1, is large enough to exceed the conversion capability of the A/D converter 22. EO5 and EO6 are error codes respectively for these conditions.

The condition 7 can be diagnosed by monitoring, from time to time, the rate of change of the output from the blood sugar sensor to time and by determing whether such rate of change exceeds a predetermined value. An error code for this condition may be EO7, for example.

The condition 8 is met when a measured value exceeds a measurement range of from 0 to 1,000 mg/dl, for example, (no proportional relationship is given between measured values and actual concentrations beyond such a range). EO8 may be used as an error code for this condition.

The condition 9 can be diagnosed as an error when the control device CC finds that no conversion coefficient is given in advance. When the condition 9 is established, an error code as of EO9 is displayed or printed.

The condition 10 is met when errors are detected for two or more out of the foregoing conditions, and has an error code of EEE.

The error codes described above are displayed or printed dependent on the results of diagnosis. When the condition 10 is met and printing is to be effected, the error code of EEE and other error codes for conditions as established are all printed.

As described above, the parts of the analyzer and the process of the chemical reaction are all self-diagnosed for determing whether they meet predetermined measuring conditions, and hence errors can be removed with ease. The blood sugar analyzer of the invention is reliable in operation and has an increased degree of measuring precision, advantages which could not be obtained by conventional manual diagnosis that tends to cause errors and oversights.

Figure 6:
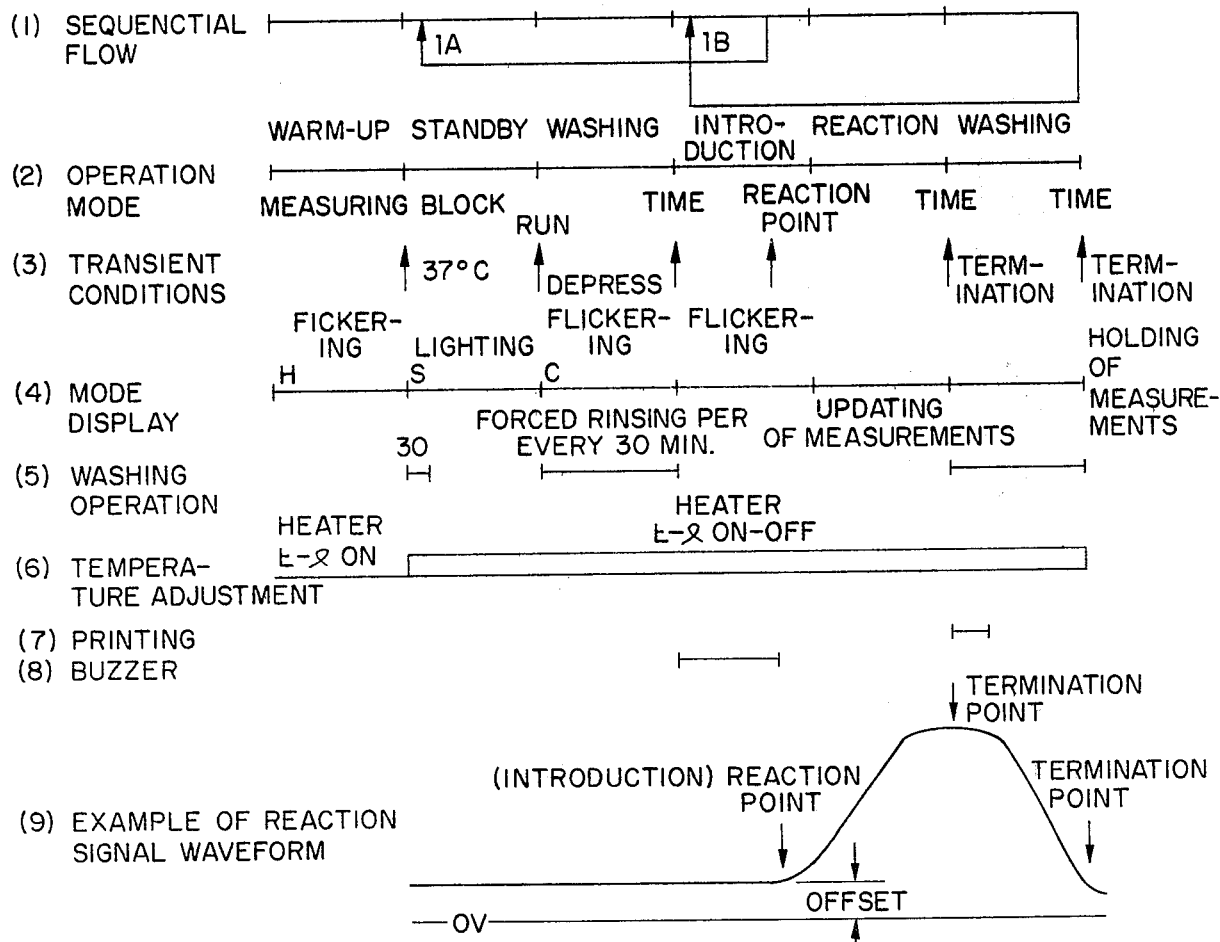
FIG. 6 is a view explanatory of the sequence of measuring operations of the analyzer of the invention.

FIG. 6 is a view illustrative of a sequence of measuring operations of the analyzer according to the present invention, FIG. 7 is a graph explanatory of transient conditions, and FIG. 8 is a graph explanatory of a process of correcting a conversion coefficient.

The present invention will now be described for its features with reference to FIGS. 3 through 8. The analyzer according to the present invention makes a measurement by going through successive conditions or steps from warm-up to standby to washing to specimen introduction to reaction to washing. The sensor block SB is heated up in the "warm-up" mode, the analyzer is ready for measurements and awaits a command therefor in the "standby" mode, the interior of the reaction cell is washed by a buffer, the introduction of a blood specimen or the like is detected (at which time a reaction starts) and the analyzer enters a next reaction condition in the "introduction" mode, and an output signal is converted into a blood sugar concentration, which is displayed, in the "reaction" mode. Once a measurement is started, the steps from specimen introduction to reaction to washing to specimen introduction are followed for successive measurements. Such a process is indicated at 1B in FIG. 6(1). These steps are indicated to the operator by symbols such as H, S, C, i as shown in FIG. 6(4).

Conditions in which the analyzer goes through the foregoing steps are as follows:

A. Warm-up to standby: The region around the sensor is in a measurable condition. For example, the region around the sensor is heated at a predetermined temperature (37° C.), and the sensor produces a stable output.

B. Standby to washing: A measurement command is issued (by depressing the operation switch $MO_2$).

C. Washing to introduction: A predetermined interval of time has passed.

D. Introduction to reaction: A starting point for the reaction of a blood specimen is detected.

E. Introduction to standby: No sample to be measured is introduced within a predetermined period of time (See FIG. 6(1) at 1A).

F. Reaction to washing: A predetermined interval of time has passed, or equilibrium of the reaction (also referred to as termination of the reaction) is reached. At this time, the value of a concentration measured is printed as illustrated in FIG. 6(7).

G. Washing to introduction: A predetermined interval of time has passed, or the rate of reduction of the output from the sensor is below a given value. When the "introduction" mode is reached, a buzzer is energized as shown in FIG. 6(8) to inform the operator that it is time to introduce a blood specimen or the like. The foregoing transient conditions are illustrated in FIG. 6(3). FIG. 6 is illustrative at (5) of forced rinsing or washing every 30 min. when the analyzer is in the standby mode of operation, at (6) of temperature adjustment for the reaction cell as effected by the heater 8, and at (9) of the waveform of a reaction signal.

Figure 3:
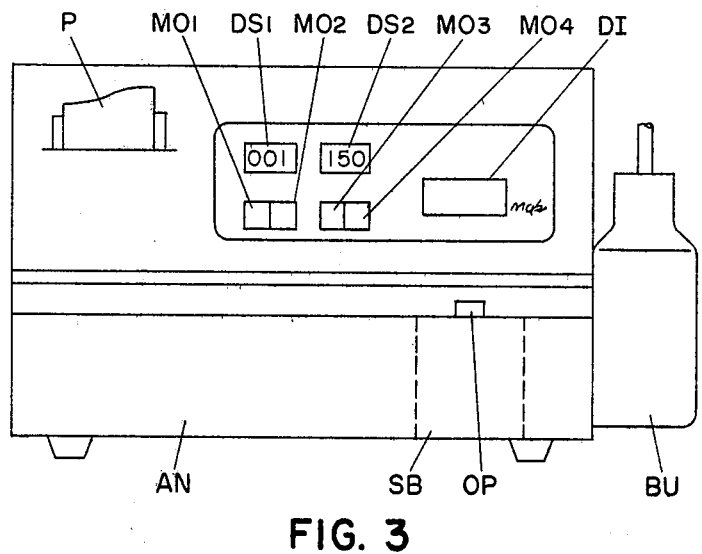
FIG. 3 is a view showing an appearance of an analyzer according to the present invention.

A reaction current is converted into a corresponding blood sugar concentration as follows:

A standard solution is first introduced, and the standard solution setting switch $DS_2$ on the control panel AN of FIG. 3 is adjusted so as to indicate the concentration in the standard solution. Then, the calibration switch $MO_1$ is depressed to start a calibration operation, and an output attained when the reaction is in equilibrium or is terminated is used to derive a conversion coefficient for converting a reaction current into a blood sugar concentration. The conversion coefficient is stored in the memory M (See FIG. 4) until a next calibration operation is carried out. Blood specimens are now measured using the conversion coefficient thus obtained to convert reaction currents into corresponding blood sugar concentrations. The conversion coefficient used and the measured concentration obtained are printed as a pair by the printer P.

The switch $MO_1$ (for commanding calibration for deriving a conversion coefficient) may be actuated at the time of either introduction, reaction, or washing. Operation of the switch $MO_1$ at the time of washing the reaction cell after the reaction has been finished is acceptable after it has been checked that the sensor produces a stable output and a sample is introduced in a proper amount, to derive a conversion coefficient in a manner described above.

The transitions from introduction to reaction to washing to introduction are automatically effected once the operation switch $MO_2$ is depressed to start a measurement, and will now be described mainly with respect to FIG. 7.

The control device CC samples an output from the blood sugar sensor 1 at constant periods Ts, and sampled values are successively stored in a memory area SR comprising a shift register. Sets of three such sampled data are taken out and processed to produce average data $\overline{V_R}, \overline{V_f}$, and the difference $(\overline{V_R} - \overline{V_f})$ between them. It is then determined whether the difference D $(\overline{V_R} - \overline{V_f})$ is larger or smaller than predetermined reference angles $\Theta_1$, $\Theta_2$ and $\Theta_3$, (or a predetermined value) to allow the analyzer to go from one mode to another. As an example, the starting point for a reaction is established when the difference D meets a relationship $D \geq \Theta_1$ wherein $\Theta_1$ is the reference angle, in which case an output at a reference point from the sensor is stored as an offset, which will be removed from a measured value to allow only a reactive quantity to be picked up, thus improving measuring accuracy. The reference point which is employed corresponds to the latest of the six data used for comparsion.

The foregoing decision process is also used for determining the points of termination of the reaction and washing. Transition from one condition to another is thus effected properly, enabling the analyzer to handle a larger number of specimens and preventing a buffer liquid from being wasted.

Correction of a conversion coefficient will be described with reference to FIG. 8.

The blood sugar analyzer is required to provide linearity between measured and actual values in a range of about from 0 to 1,000 mg/dl. It is known that when the analyzer is calibrated using a standard solution having a high blood sugar concentration of about 500 mg/dl, the result of analysis is overvalued, i.e. larger than an actual concentration in a lower concentration range, and conversely, when the analyzer is calibrated using a standard solution having a lower blood sugar concentration of about 150 mg/dl, the result of analysis is undervalued, i.e. smaller than an actual concentration in a higher concentration range. To cope with such a problem, calibration is first effected using a standard solution having a low blood sugar concentration of about 150 mg/dl to derive a correction coefficient $K_L$. Using such a correction coefficient in a higher concentration range would cause the results of analysis to be shifted to the negative side. Therefore, calibration is also effected using a standard solution having a high blood sugar concentration of about 500 mg/dl to derive a correction coefficient $K_H$. Use of two different correction coefficients causes calibration results to differ in the vicinity of the blood sugar concentration of 300 mg/dl where there is a changeover between the two correction coefficients. Between the correction coefficients $K_L$, $K_H$, there is employed another correction coefficient $K\alpha$ which is obtained by proportionally distributing the difference between the correction coefficients $K_L$, $K_H$ according to blood sugar concentrations.

Linear correction is thus possible as indicated by the dot-and-dash line in FIG. 8. In FIG. 8, a horizontal axis indicates actual blood sugar or glucose concentrations, a vertical axis indicates sensor outputs, conversion coefficients, and calculated values, and SO is a characteristic curve for the sensor outputs.

In order for the blood sugar analyzer to effect correct measurements, it is necessary to monitor parts of the analyzer involved in measurements and the process of a reaction, and to make a diagnosis to see if results of such monitoring meet predetermined measuring conditions.

According to the present invention, outputs from the blood sugar sensor 1 and the temperature sensor 7 are utilized to monitor various items, such as the temperature in the reaction cell CE, the degree of stabilization of sensitivity of the electrode 1, the degree of deterioration of the fixed enzyme membrane, the amount of an offset and a variation thereof, and to make a diagnosis to ascertain whether the analyzer is in proper analyzing operation based on results of the above monitoring. The analyzer includes the printer P which serves as a monitor means to print out different types of maintenance information, resulting in easy maintenance and collection of diagnosis information. The diagnosis information is printed out from item to item to enable easy removal of the causes of errors.

The present invention has the following advantages:

1. Modes of sequential operation of the analyzer are displayed with encoded symbols (such as H, S, C, i, for example) to facilitate control of the analyzer.

2. Transient conditions in the analyzer are all determined by the microcomputer to increase the handling capability of the analyzer and to prevent the buffer liquid from being wasted.

3. Conversion coefficients can easily be obtained simply by depressing the calibration switch even under the control of an unskilled operator.

4. Corrected conversion coefficients are given in respective measurable ranges, and hence linearity and reproducibility are available in a wide range of measurements.

5. The analyzer has a self-diagnosing function for increased reliability and to provide suitable information as to when replacement of the blood sugar sensor is necessary.

6. The analyzer has a maintenance function which reduces the labor and time required for manual maintenance.

The temperature detecting system according to the invention will now be described. A region in the vicinity of the blood sugar sensor needs to be maintained at a predetermined temperature since the rate of chemical reaction which takes place in the analyzer is susceptible to and dependent upon the temperature value. Also, it is preferable to measure blood specimens at a temperature which is substantially the same as the temperature of the body of the human being or animal from which the blood specimens are taken.

FIG. 9 is a graph showing a characteristic curve of the output of a temperature sensor as a function of temperature.

Heretofore, a temperature sensor has had a measurable temperature range from the absolute zero (about $-273°$ C.) to 270° C. and has been capable of producing outputs (from 0 volts to about 6 volts) indicative of measured temperatures in that range. A voltage indicating a target temperature to be controlled (corresponding to about 37° C., for example, which is the temperature of a human body) has been selected from the range of such sensor outputs. However, it is generally difficult to establish a temperature near 37° C. in such a wide temperature range (the smaller the temperature to be set in the measurable temperature range, the more difficult it is to establish such a desired temperature), and hence, high precision temperature control has been difficult to achieve.

According to the invention, only an output from the temperature sensor which is in the vicinity of the target temperature or range thereof is picked out, and other outputs from the temperature sensor which are unnecessary for temperature control are cut off, thus eliminating the prior difficulty. The embodiment according to the invention resides in the provision of a differential amplifier for differentially processing an output from a temperature for measuring the temperature of a body to be measured and a predetermined value so as to change the latter into agreement with a controlled target temperature.

Figure 11:
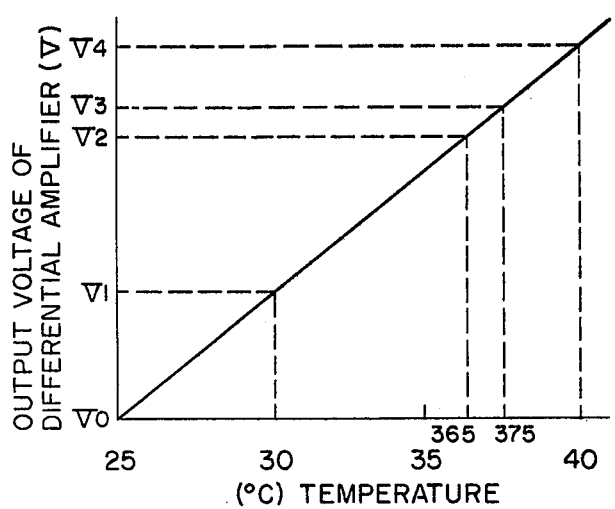
FIG. 11 is a graph showing output characteristics of the temperature detecting system shown in FIG. 10.

FIG. 10 is a block diagram showing a central arrangement of the embodiment, and FIG. 11 is a graph illustrating the temperature-dependent output characteristics of a temperature detecting means according to the present invention.

A temperature sensor 7 produces an output voltage which is compared by a differential amplifier 30 with a given voltage $V_0$, with only the difference therebetween being amplified and converted by a temperature encoder 31 into temperature codes $TC_1$ through $TCL_4$. The temperature encoder 31 is composed mainly of comparators $CO_1$ through $CO_4$, each having one input supplied with the output from the differential amplifier 30 and the other input supplied with a different one of given voltages $V_1$ through $V_4$. A limiter 32 serves to cut off a negative voltage generated by the differential amplifier 30 when the output voltage from the sensor 7 is below a predetermined voltage, $V_O$, for example. A zener diode Z serves to prevent an excessively large output of the differential amplifier 30 from being applied to the comparators $CO_1$ through $CO_4$. Designated at $R_1$ through $R_{18}$ are resistors, and at C is a capacitor.

Assuming that $V_O$ is voltage corresponding to 25° C., and $V_1$ through $V_4$ are voltages corresponding to 30° C., 36.5° C., 37.5° C. and 40° C., respectively, the comparator $C_1$ produces a high (H) logic level output signal when the output from the temperature sensor 7 is below 30° C. and low (L) logic level output signal when the output from the temperature sensor 7 exceeds 30° C. The comparators $CO_2$, $CO_3$, and $CO_4$ produce high (H) logic level output signals when the output of the temperature sensor 7 exceeds 36.5° C., 37.5° C., and 40° C., respectively. Therefore, when the temperature measured by the sensor 7 is below 30° C., only the output $TC_1$ from the comparator $CO_1$ goes to a high logic level. When the output of the sensor 7 is in the range of from 30° C. to 36.5° C., all of the outputs $TC_1$ through $TC_4$ go low. Only the output $TC_2$ is at a high logic level when the temperature detected by the sensor 7 ranges from 36.5° C. to 37.5° C. The outputs $TC_2$ and $TC_3$ go high when the temperature detected by the sensor 7 ranges from 37.5° C. to 40° C. When the output from the sensor 7 is indicative of 40° C. or higher, the outputs except $TC_1$ from the comparators are held at a high logic level. The foregoing is summarized in tabular form as follows:

| Tempera-<br>ture Codes | Temperature (°C.) | | | | |
| --- | --- | --- | --- | --- | --- |
| | Below<br>30 | 30-36.5 | 36.5-37.5 | 37.5-40 | Over<br>40 |
| $TC_1$ | H | L | L | L | L |
| $TC_2$ | L | L | H | H | H |
| $TC_3$ | L | L | L | H | H |
| $TC_4$ | L | L | L | L | H |

The voltages $V_1$ through $V_4$ can be established, with the voltage $V_O$ serving as a reference, more easily and correctly than in the conventional system in which a set value has been determined taking into consideration the range of all measurable temperatures. The preamplifier or differential amplifier 30 can be adjusted to increase its gain and hence its differential output, thereby making its output greater for each temperature unit, with increased resolving power. The temperature and the output from the differential amplifier have a relationship as shown in FIG. 11, in which a desired portion or range can be taken out or enlarged, an arrangement which differs from that of FIG. 9. Therefore, the system of the invention has an increased temperature resolving power i.e. resolution, for more correct measurements.

The control device equipped with a microcomputer detects the temperature in the measuring cell in the blood sugar analyzing unit BSU on the basis of the temperature codes $TC_1$ through $TC_4$. When the temperature is below 36.5° C., for example, the control device energizes a heater. When the temperature is in the target temperature range of from 36.5° C. to 37.5° C., the control device determines such temperature as appropriate for a measurement and effects measurement of a blood sugar concentration. When the temperature is over 37.5° C., the heater is turned off until the interior of the measuring cell is cooled to a desired temperature. When the temperature is below 36.5° C. or over 40° C., the control device determines that a correct measurement is impossible, and effects no measurement of a blood sugar concentration.

While in the foregoing embodiment the comparison voltage $V_1$ through $V_4$ has been so defined as to keep the interior of the measuring cell at a temperature in the vicinity of 37° C., the present invention is not limited to the disclosed numerical values.

With this embodiment, only a signal in the vicinity of a reference temperature is taken out for temperature detection, so that the temperature resolving power is increased, the reference value can be established with ease, and correct temperature control is rendered possible.

A system according to the invention for removing an offset from an output of a differential amplifier will now be described. High reliability, reproducibility, and linearity are required of an analog circuit including an A/D converter over a wide range of blood sugar concentrations (for example, from 1 to 1,000 mg/dl) in blood sugar analyzers with which the present invention is concerned. Removal of an offset (including noises, a bias, and others), from the output of an analog amplifier, plays a vital role in increasing accuracy with which glucose concentrations are measured.

Figure 4:
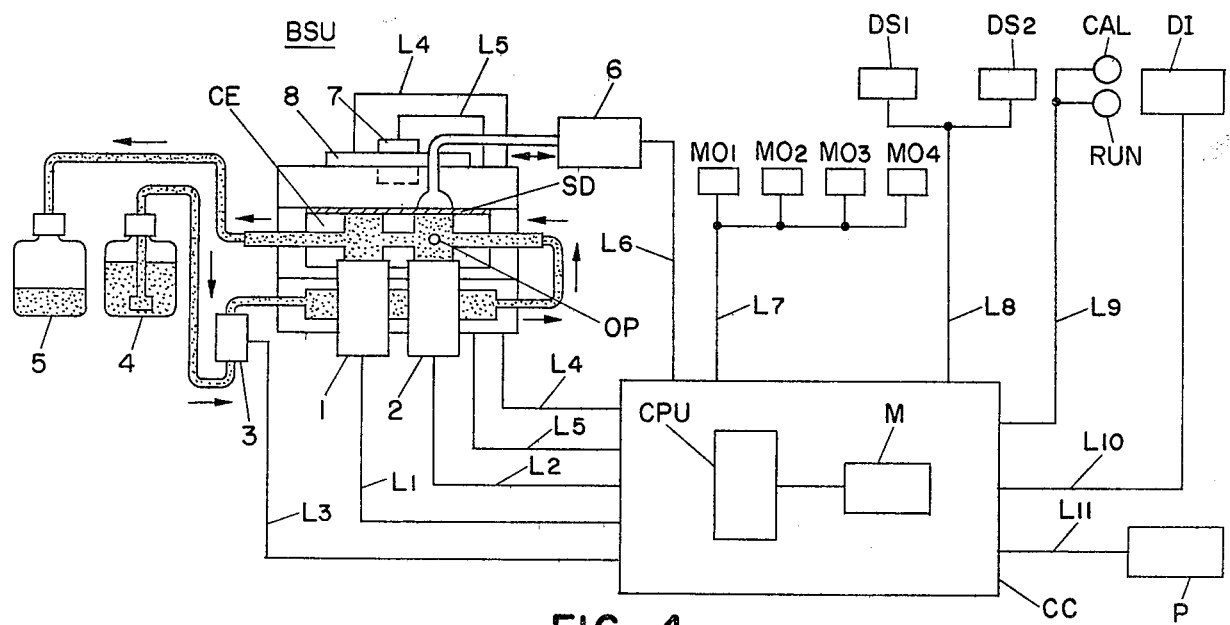
FIG. 4 is a view illustrating an overall arrangement of the analyzer of the present invention.
Figure 5:
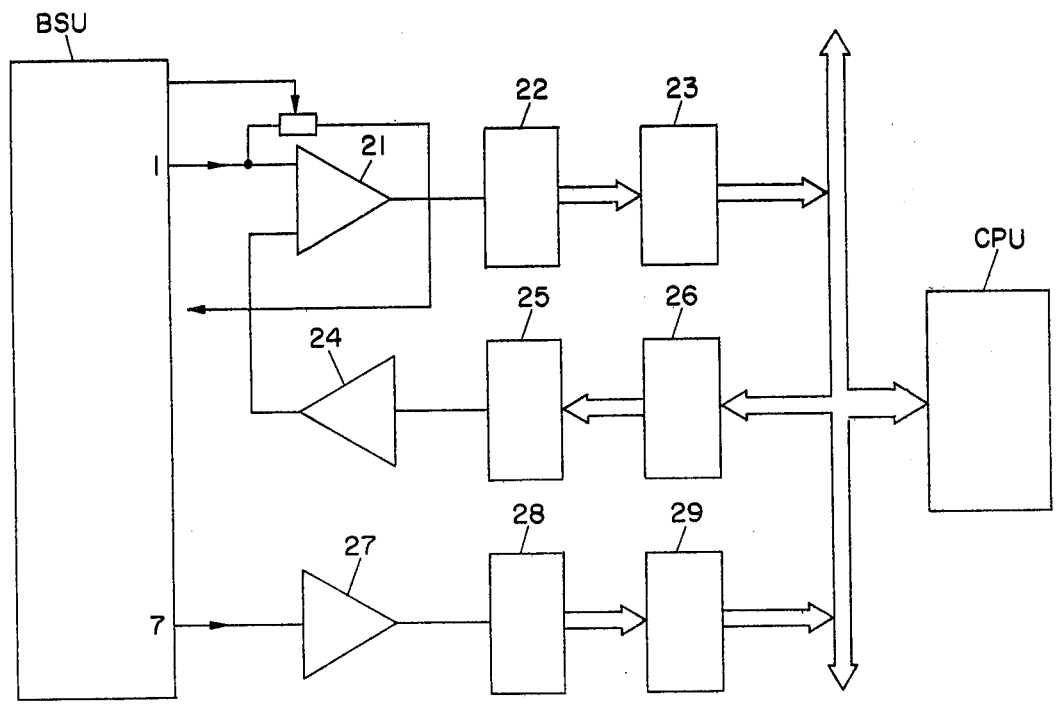
FIG. 5 is a block diagram of a control device.
Figure 12:
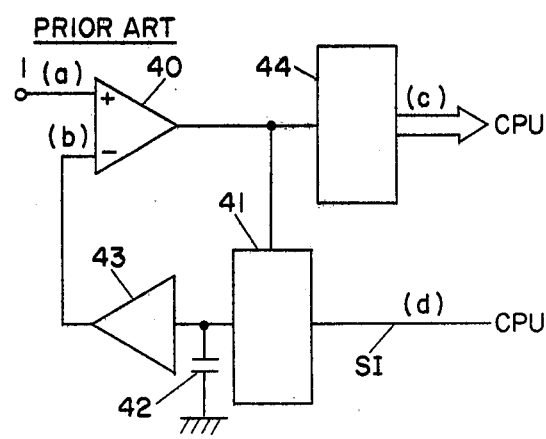
FIG. 12 is a block diagram of a conventional offset removing system.
Figure 13:
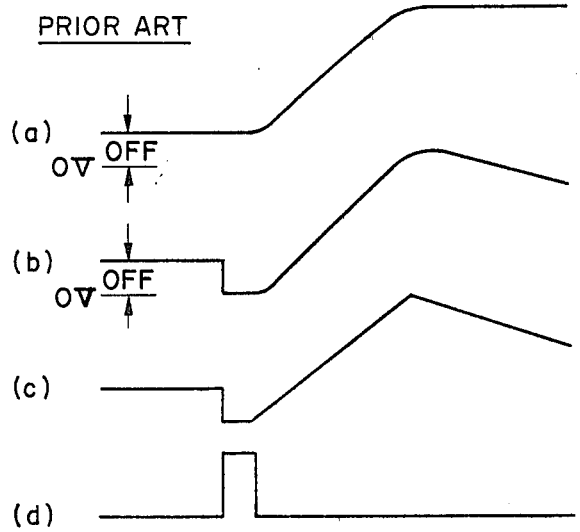
FIG. 13 is a timing diagram showing the waveforms of signals generated in the system of FIG. 12.

FIG. 12 is a block diagram of a conventional system for removing an offset, and FIG. 13 is a timing diagram showing waveforms of signals generated in the blood sugar analyzer of FIG. 4.

The system shown in FIG. 12 comprises a differential amplifier 40 for amplifying the difference between an analog input signal from a measuring electrode 1 and an offset, an A/D converter 44 for converting an analog signal from the differential amplifier 40 into a digital signal, and a sampling switch 41 responsive to a sampling command signal SI, either supplied from a control circuit CPU (not shown) or set manually, for storing the offset in a hold circuit comprising a capacitor 42 and a buffer amplifier 43.

An analog input signal as shown at (a) in FIG. 13 is amplified with a certain constant by the differential amplifier 40, which supplies its output to the A/D converter 44 and the sampling switch 41, which have initially been fed with the offset only as shown in FIG. 13. The A/D converter 44 converts the amplified analog signal into a digital signal. The sampling switch 41 allows the amplified analog signal to be transferred into and held in the hold circuit only when the sampling switch 41 is supplied with the sampling command signal SI. When an analog input signal corresponding to a reaction current is thereafter supplied, the differential amplifier 40 subtracts the offset from the input signal to produce only a signal component, which is then converted by the A/D converter 44 into a digital signal that will be converted by the control circuit into a blood sugar concentration value as expressed in a predetermined unit for display.

The sample hold circuit, comprised of the capacitor 42 and buffer amplifier 43, has a limited hold time which gives rise to a phenomenon that allows a held signal to be released as indicated by the downward slant at (b) in FIG. 13 when the reaction is in a steady condition or is terminated. Such a phenomenon is caused by the discharging of the capacitor 42 through the amplifier.

Where a sample hold signal is to be set manually, the operator is likely to forget to actuate the switch, resulting in an entirely incorrect measurement and rendering the measured result useless. With automatic removal of an offset under the control of the control circuit, an offset may exceed half of a signal component during a reaction in which case only a limited amount can be measured and at times measurement is not rendered possible. To cope with this, the number of bits for the A/D converter may be increased for an improved resolving power. However, an A/D converter thus modified is quite costly.

It is an object of this embodiment to overcome the prior problem as described above by holding and removing an offset signal in a more precise and accurate manner.

According to this embodiment, a memory means is provided for holding an offset to prevent the latter from being varied with time, which would take place with the capacitor and amplifier used, and a control circuit equipped with a microcomputer which serves to monitor at all times an analog input signal (reaction current) variable with time for determining an optimum offset, permitting only a signal component to be supplied to an A/D converter for effective use of the latter.

Figure 14:
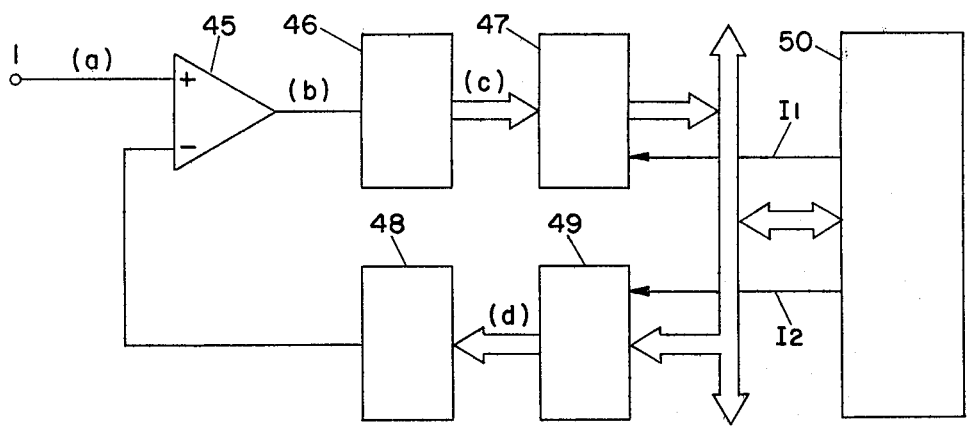
FIG. 14 is a block diagram of an offset removing system according to still another embodiment of the present invention.

This embodiment will be described with reference to FIGS. 14 and 15. FIG. 14 is a block diagram of the embodiment, and FIG. 15 is a timing diagram showing waveforms of signals generated in the system of FIG. 14.

Figure 15:
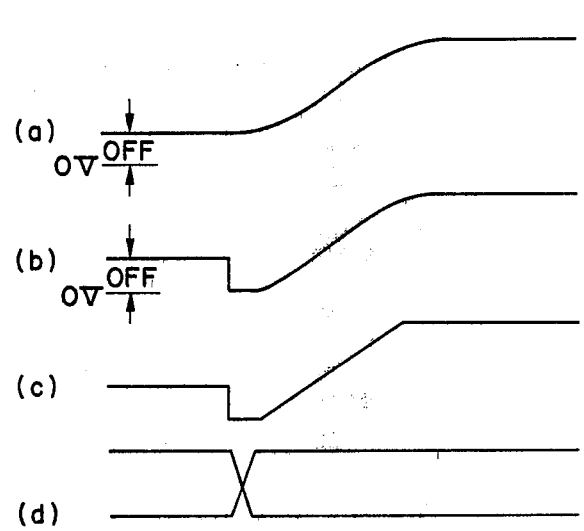
FIG. 15 is a timing diagram showing the waveforms of signals generated in the system of FIG. 14.

The system shown in FIG. 15 comprises a differential amplifier 45 for amplifying the difference between an analog input signal from a measuring electrode 1 and an offset signal, an A/D converter 46 for converting an analog output signal from the amplifier 45 into a digital signal, a control circuit 50 for receiving the digital signal from the A/D converter 46 via a buffer 47 to process and control the received digital signal, a data latch 49 responsive to a control signal from the control circuit 50 for storing and reading out an offset, and a digital-to-analog (D/A) converter 48 for converting the offset, read out from the data latch 49, into an analog signal and for supplying the latter to the differential amplifier 45.

Operation of the system thus constructed will be described with reference to FIGS. 14 and 15. An analog input signal as shown at (a) in FIG. 15 from the fixed enzyme membrane sensor 1 is amplified with a certain constant by the differential amplifier 45, which produces an output as shown at (b) in FIG. 15 that is supplied to the A/D converter 46. The A/D converter 46 converts the supplied analog signal into a digital signal as illustrated at (c) in FIG. 15. The digital signal is transferred via the buffer 47 and a data bus and stored at a predetermined region in a memory in response to a command signal $I_1$ from the control circuit 50. The digitial signal is also delivered to a command signal $I_2$ from the control circuit 50. An offset that has been held in the data latch 49 is read out of the data latch 49 by the command signal $I_2$, and converted by the D/A converter 48 into an analog signal, which is supplied as an input to the differential amplifier 45.

When there is no blood sample introduced in the sensor, that is, when the analog input signal is zero, the differential amplifier 45 delivers an offset as its output (See FIG. 15 at OFF) which is converted into a digital signal. The digital signal is supplied to the control circuit 50 and simultaneously stored in the data latch 49 under the control of a command from the control circuit 50. When a blood sample to be measured is introduced, a chemical reactor starts, and as the latter progresses the sensor produces an analog signal proportional to the blood sugar concentration in the blood sample. Since the offset that has been stored in the data latch 49 is converted by the D/A converter 48 into an analog signal which is delivered as an input to the differential amplifier 45, the A/D converter 46 receives as its input a signal having a value indicative only of a reactive analog quantity that is in proportion to the blood sugar concentration in the blood sample.

Subsequently, the input signal as it varies with time through the progress of the reaction is monitored by the control circuit 50. When the control circuit 50 automatically detects a starting point of the reaction of the blood sample, the control circuit 50 causes the data latch 49 to store an amount of offset at that time as a final offset. A signal having a value indicative of the amount of blood sugar which is reacting can be obtained by subtracting the offset at the reaction starting point from the reaction signal as it increases progressively. The signal as it is supplied when the reaction becomes steady is converted by the control circuit 50 into a quantity in the unit if mg/dl, which is then indicated on the display DI (FIG. 4) as a blood sugar concentration.

The foregoing process can be applied to a situation in which the reaction signal increases. A process for a situation in which the reaction signal decreases will be described. Each time that measurement of one blood sample is finished, a measuring block (not shown) in the blood sugar analyzer is washed in preparation for measurement of a next blood sample. The blood sample previously measured is washed away, and the reaction signal is reduced in intensity. However, the reduced signal level will not necessarily be brought back to the level at the reaction starting point for various reasons, such as a lessened sensitivity of the sensor and temperature changes, for example. Thus, the amount of offset produced after the blood sample has been washed away is likely to differ from that generated before the reaction occurs. If the offset level after the washing has been finished is reduced below the offset level prior to the starting of the reaction, notwithstanding the analyzer having been set to have the offset fixed at the level prior to the reaction process, an offset tends to be excessively large at a low reaction signal level during measurement of a next blood sample, resulting in a possibility for a measured quantity to become negative. According to the present invention, a reaction signal as it is lowered is also monitored from time to time, and when the reaction signal becomes smaller than an offset level prior to the reaction, the offset level is changed or lowered to prevent the reaction signal from becoming smaller than the offset level. With this arrangement, an A/D converter is not required to be so constructed as to provide against a negative input, and hence an inexpensive A/D converter that is responsive only to positive inputs is all that is needed.

With this embodiment, an offset is held in a data latch, and hence will not be reduced in intensity with time resulting in a maintained measuring accuracy. A reaction signal from a sensor is monitored at all times by a control circuit for determining an optimum offset level so that an A/D converter will not be supplied with positive and negative input signals, but with a positive component only. Therefore, an inexpensive A/D converter will suffice for use in the system according to the embodiment, all without the need for a high-performance, costly A/D converter having increased number of bits to provide for both positive and negative inputs.

An analog gain control system in accordance with the present invention will now be described. Blood sugar analyzers to which the present invention is directed include an analog circuit with an A/D converter having high reliability, reproducibility, and linearity over a wide range of blood sugar concentrations (for example, from 1 to 1,000 mg/dl).

The enzyme membrane sensor has its sensitivity variable due to deterioration with time and sensor replacement. To cope with such sensitivity variations, it has been prior practice to either use a high-precision A/D converter with an increased number of conversion bits, or provide the amplifier with a manually operable gain adjuster for adjusting the gain of the amplifier each time a measurement is made until an input to the A/D converter attains a predetermined level range.

However, the former conventional attempt is uneconomical because a high-precision A/D converter must be employed, and the latter expedient is disadvantageous because an adjustment operation required is tedious.

Figure 16:
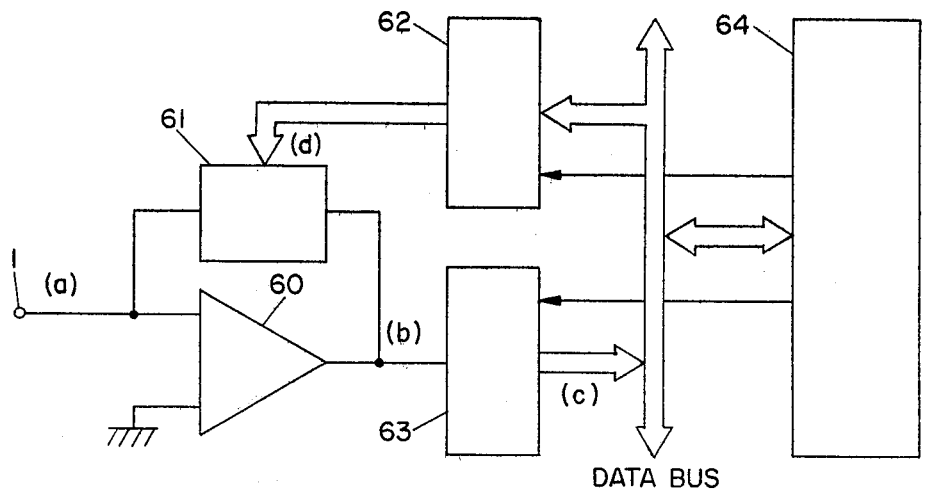
FIG. 16 is a block diagram of a gain controlling system according to still another embodiment of the present invention.
Figure 17:
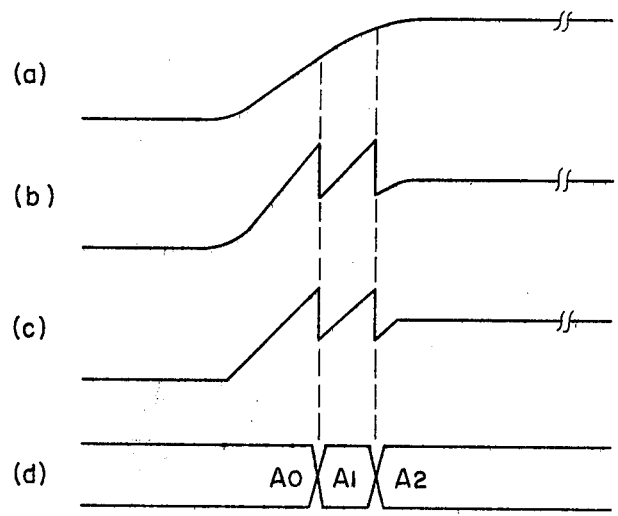
FIG. 17 is a timing diagram showing the waveforms of signals generated in the system illustrated in FIG. 16.

According to this embodiment, the gain of an amplifier can be automatically adjusted to dispense with tedious manual adjustment operation, while also using an A/D converter which need not be of the high-precision type, thus overcoming the conventional difficulties. FIG. 16 is a block diagram of a system according to this embodiment, with data lines and control signal lines indicated by thick and thin arrows, respectively, and FIG. 17 is a timing diagram illustrating various waveforms of signals generated in the system of FIG. 16.

The system shown in FIG. 16 comprises an amplifier 60 for amplifying a reaction current supplied from the fixed enzyme membrane sensor 1 and for converting the amplified current into a corresponding voltage, a D/A converter 63 for converting an analog signal from the amplifier 60 into a digital signal, a control circuit 64 equipped with a microcomputer for receiving the digital signal, and a group of gain control switches 61 for controlling the gain of the amplifier 60 upon reception of data from the data latch 62 in response to a control signal supplied from the control circuit 64.

Operation of the system will now be described. A reaction current (shown at (a) in FIG. 17) detected by the fixed enzyme membrane sensor 1 is increased when a reaction is started, and reaches a steady condition at the termination of the reaction upon elapse of a predetermined period of time. The reaction current is supplied as an input signal to the amplifier 60 in which the current is amplified with a constant whose value is determined by a selected one of the switches in the group 61. An output signal from the amplifier 60 having a waveform (b) as shown in FIG. 17 is delivered to the A/D converter 63 which converts the signal into a digital signal (as shown at (c) in FIG. 17), which in turn is fed to the control circuit 64. The control circuit 64 ascertains whether the input level (shown at (b) in FIG. 17) of the A/D converter 63 is lower than the predetermined range (that is, when the input level is in the range capable of producing large conversion errors), the control circuit 64 increases the gain of the amplifier 60, and when the input level of the A/D converter 63 is higher than the given range, the amplifier 60 is controlled so as to have a decreased gain. Stated otherwise, the data latch 62 is responsive to a control signal from the control circuit 64 to produce as an output a gate selection code as shown at (d) in FIG. 17, which illustrates combined code signals on a plurality of lines. The gate selection code produced serves to select one switch out of the grouped switches 61 for controlling the gain of the amplifier 60. The gain of the amplifier 60 is controlled stepwise by the gain control switch so that the amplifier 60 produces an output signal (shown at (b) in FIG. 17) which is caused by the gain selection code to have a sawtooth waveform as shown at (c) in FIG. 17.

While in the foregoing embodiment an analog output signal from the blood sugar analyzer is converted into a digital signal, the system will find wide general use for converting analog signals, other than those from blood sugar analyzers, into digital signals.

Although the group of gain control switches has been used which is easily controllable by a microcomputer for changing the gain of the amplifier in a stepwise manner, the gain of the amplifier may instead by changed in a smooth manner by an arithmetical circuit.

With the above-described embodiment, a control circuit comprising a microcomputer monitors an output from a sensor for automatic control and adjustment of the gain of an amplifier, bringing the input level of the analog-to-digital converter into a good range at all times. Therefore, manual adjustment is unnecessary, and an inexpensive A/D converter with only limited functions can be used for high-precision measurements.

A time monitoring and controlling system in accordance with the present invention will now be described. As described above with reference to FIG. 6, a blood sugar analyzer makes measurements while going through various modes of steps such as from warm-up to standby to cell washing to sample introduction to reaction to cell washing. These steps or conditions are indicated by illuminating, constantly or intermittently, various lamps to inform the operator of the mode or condition of the analyzer. It is necessary to monitor and control various intervals of time, such as the time interval in which a sample is washed away after it has been measured, the time interval in which a sample reacts, the time interval for lighting lamps, or the cycling time interval for intermittently illuminating the lamps, i.e. the frequency of blinking.

Figure 18:
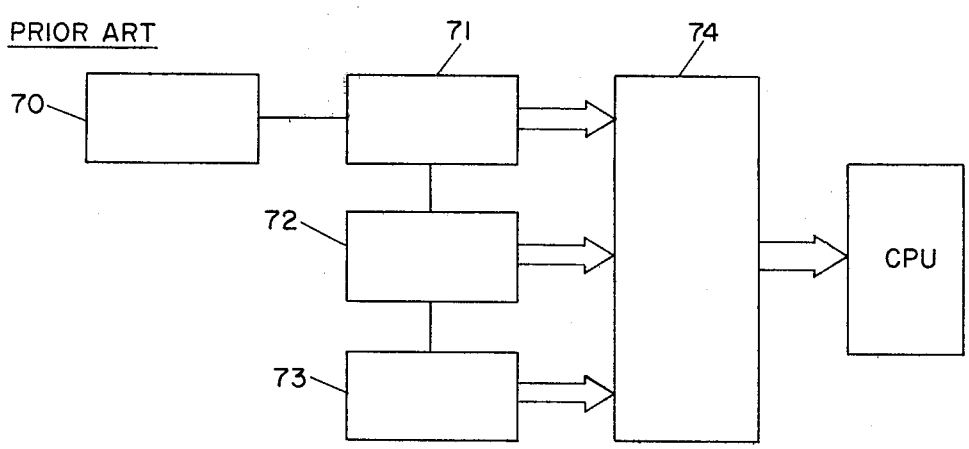
FIG. 18 is a block diagram of a conventional time monitoring and controlling system.

FIG. 18 is a block diagram of a conventional time monitoring system. The conventional time monitoring system comprises an oscillator 70 for exclusive use in the system, frequency dividers 71, 72, and 73 comprised of counters, a decoder 74, and a microcomputer CPU. A clock signal from the oscillator 70 is frequency-divided by the frequency dividers 71, 72, and 73 into signals having various frequencies. Signals having predetermined frequencies are delivered through the decoder 74 to the microcomputer CPU, in which the supplied various frequency signals are determined by an interval decision logic circuit (not shown) for a variety of time monitoring and controlling operations under the control of a sequence program using results of determination.

The conventional system is disadvantageous in that its circuit arrangement is complex and costly as it comprises frequency dividers, a decoder, a decision logic circuit, and other elements.

It is an object of this particular embodiment of the invention to provide a simple and inexpensive time monitoring and controlling system by employing a microcomputer to effective use therein.

Figure 19:
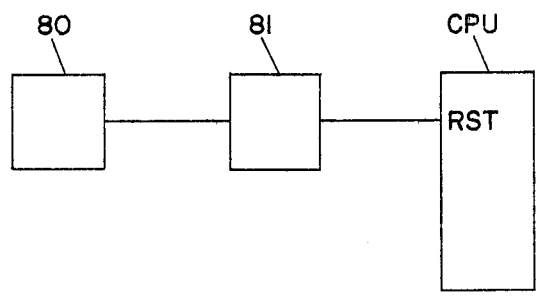
FIG. 19 is a block diagram of a time monitoring and controlling system according to still another embodiment of the present invention.
Figure 20:
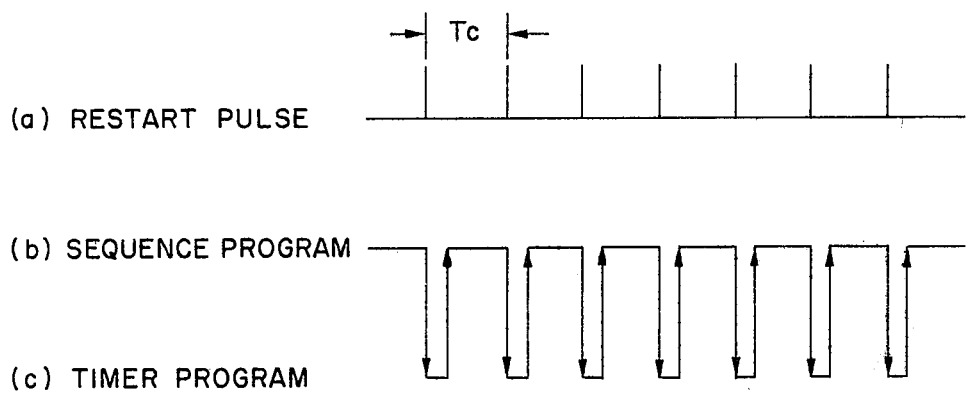
FIG. 20 is a timing diagram of the waveform of a signal generated in the system of FIG. 19.

This embodiment will now be described with reference to FIGS. 19 and 20, wherein FIG. 19 is a block diagram of a system according to the embodiment, and FIG. 20 is a timing diagram showing waveforms of signals in the system of FIG. 19.

The system of FIG. 19 comprises an oscillator 80 for producing a clock signal having a predetermined frequency (1/TC), a waveform shaping circuit 81 comprising a shift register, gates and other components, and a microcomputer CPU. The clock signal is differentiated by the waveform shaping circuit 81, which supplies a signal having a waveform (a) (FIG. 20) to a terminal RST (restart) of the microcomputer CPU as a restart command signal (interrupting signal). When the signal (a) is fed to the microcomputer CPU, the microcomputer CPU interrupts a main sequence program as shown at (b) in FIG. 20 and is transferred to the mode of operation under the control of a timer or timing program as shown at (c) in FIG. 20. At this time, the sequence program causes a memory to store various data on time intervals required for the analyzer, such as, for example, a flickering cycle for indicating lamps, a time interval in which a sample reacts, and a time interval in which a sample is washed away after it has been measured. The timing program allows the various time data stored in the memory to be counted or subtracted from a starting point at which a restart pulse is received, and to be updated successively. When a certain time data falls to zero, (upon elapse of a predetermined period of time), the sequence program detects such a condition and produces a prescribed control signal for shifting the control of the analyzer from one mode to another mode of operation. The sequence program contains individual programs for monitoring time data stored in the memory to enable various time measuring and controlling operations. The restart pulse has a cycling time $T_C$ which is longer than an execution time for the timer program for effecting time measurement. The time data are stored in the memory as they are converted, with the restart pulse $T_C$ serving as a reference.

With this embodiment, the system does not require expensive devices such as time measuring frequency dividers, a decoder, and a decision logic circuit, and hence is less costly and more simple in construction. Time is measured by a timer program used exclusively for time measurement, and not by a main sequence program, which is therefore less burdened, which results in an increased handling capability for the microcomputer.

A means for determining control functions in accordance with the present invention will be now described. The blood sugar analyzer according to the present invention can monitor the progress of a reaction in the cell as described above. When an operator decides to adjust the measuring sensitivity in the course of the measurement, he should depress a control switch for indicating the mode of operation of the analyzer to prevent the analyzer from being released from the process of the reaction or from being shifted to another mode of operation while the sensitivity is being adjusted. Such a controlling operation is necessary to avoid a condition in which the blood specimen or the like starts being washed away when termination of the reaction is detected.

A conventional control switch for giving such a command is usually separate from a control switch for starting a measurement. The separate control switch however takes up a space of its own and results in a complex structure. It is preferable to use a single control switch for producing commands for different functions or control operations. Such a demand can be met by providing a control device with decision means for detecting the operation of a switch and for determining which function is indicated by such an operation of the switch in order to give the switch a plurality of functions.

Figure 21:
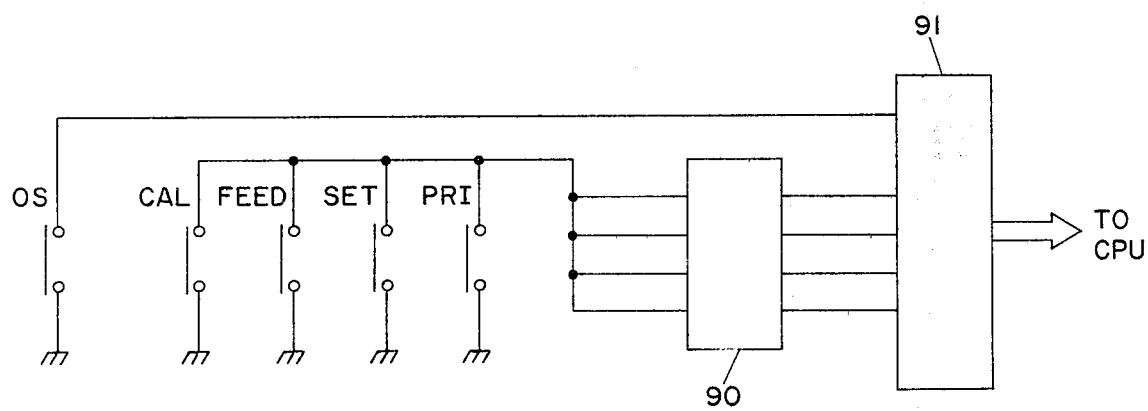
FIG. 21 is a fragmentary circuit diagram of a means for determining control functions according to still another embodiment of the invention.

An embodiment of such decision means in accordance with the present invention will now be described, with reference to FIG. 21, which is a block diagram of such a decision means. According to the present invention, a control switch OS is connected through a buffer 91 to a microcomputer CPU, and can produce a predetermined command when actuated. Designated at 90 is a latch, and at CAL, FEED, SET, and PRI are mode indication switches for indicating various modes of operation, such as calibration, paper feeding for a printer, setting of specimen numbers, and printing operation, respectively.

When the control switch OS is actuated, a blood specimen or the like is introduced to start a measuring operation. Upon introduction of the blood specimen or the like, a chemical reaction takes place between the blood specimen or the like and the fixed enzyme membrane, and a current due to the chemical reaction flows in the measuring electrode. The microcomputer CPU computes a blood sugar concentration value on a seven-segment display periodically. When the reaction reaches an equilibrium condition (a predetermined interval of time after the reaction has started), the blood sugar concentration value displayed at that time is printed out by the printer. Calibration using a standard sample has already been carried out. The operator monitors the display until the blood sugar concentration variable from time to time reaches a stable value. When an operator finds that the sensitivity of the measuring electrode is not optimum in the meantime, he can depress the switch OS which has started the measuring operation which will hold the condition of the analyzer in its present mode of operation and will prevent against transfer to other modes of operation (called a "hold-free function"). Such an operation is detected by a decision means in the microcomputer, and is identified as an operation after a measurement has been started or as a second operation, whereupon the microcomputer CPU releases the analyzer from the measuring operation. The decision means may comprise an RS flip-flop or other similar component. The operator can adjust the sensitivity of the blood sugar measuring electrode by adjusting the gain of an amplifier connected to the output of the blood sugar measuring electrode. Such an adjustment operation can be carried out easily since the output from the amplifier is displayed as it is converted by the microcomputer periodically into a corresponding blood sugar concentration. The control switch OS can be actuated again, which will allow the analyzer to return from the released condition (hold-free condition) to the measuring mode of operation. the control device will identify such switch actuation being subsequent to the releasing of the analyzer, thereby permitting the analyzer to enter the measuring operation again.

With the embodiment as described above, different modes of operation, such as starting measurement, releasing the analyzer from a measuring operation, and causing the analyzer to enter the measuring mode of operation again, can be selected by a single switch which takes up only a small amount of space for attachment and is easily actuatable.

Various concepts according to the present invention, such as temperature detection or correction of an offset in an output from a differential amplifier can effectively be applied to apparatus other than blood sugar analyzers.

From the foregoing, it will be observed that numerous variations and modifications may be effected without departing from the true spirit and scope of the novel concept of the invention. it is to be understood that no limitation with respect to the specific embodiments illustrated herein is intended or should be inferred. It is, of course, intended to cover by the appended claims all such modifications as fall within the scope of the claims.

What is claimed is:

1. A blood sugar analyzing apparatus having a reaction cell which houses a fixed enzyme membrane sensor and a measuring electrode and which receives a blood specimen, said fixed enzyme membrane sensor measuring the blood sugar concentration in the blood specimen as a function of a reaction current signal generated in the sensor by the chemical reaction, and means for calculating a reaction current offset for adjusting the measured reaction current value to more accurately detect the actual blood sugar concentration by subtracting said offset from said measured reaction current value; and said apparatus having monitoring means for sensing a plurality of operational values including reaction cell current, reaction cell temperature and reaction current offset, to compare said sensed values with predetermined corresponding ranges, and to display an error signal when at least one of said values exceeds it corresponding range, to thereby provide information concerning operation conditions and maintenance needs to an operator.

2. The apparatus as set forth in claim 1 wherein the monitoring means further comprises means for sensing the temperature near the chemical reaction in the reaction cell and for producing a sensor output signal having a value proportional to the sensed temperature, means for comparing the sensor output signal value to a value corresponding to a target temperature and for producing a differential output signal indicative of the difference between the sensed and target temperature, and means for converting the differential output signal into coded output signals indicating which one of several exclusive ranges said sensed temperature falls within, means for controlling a heater to maintain the specimen in the temperature range which includes the target temperature in response to said coded output signals, and wherein measurement of blood sugar concentration is effected only when the sensed temperature is within the range which includes the target temperature as indicated by a corresponding coded output signal.

3. The apparatus as set forth in claim 1 further including means for removing an offset signal from the reaction current signal comprising:

a differential amplifier which receives the reaction current signal in the form of an analog input signal at a first input and having a second input;

an A/D converter for converting the output from said differential amplifier into a digital output signal;

a control circuit for monitoring said analog input signal and for detecting when said analog input signal falls to a value of about zero and for generating a control signal in response to the analog input signal reaching a predetermined value;

memory means for storing an offset portion of said differential amplifier output signal in the form of a digital output signal generated by said A/D converter when the control circuit detects the analog input signal falling to a value of about zero;

a D/A converter for converting the offset portion stored in said memory means into an analog signal and for supplying said analog signal into the second input of the differential amplifier in response to a control signal from said control circuit;

and wherein the differential amplifier removes a signal from the analog input signal corresponding to the offset portion.

4. The apparatus as set forth in claim 1 further including an amplifier with means for adjusting the gain thereof for amplifying an analog input signal from said reaction current signal;

an A/D converter for receiving the output signal from said amplifier and for converting said output signal into a digital signal;

a control circuit for determining whether the output from said amplifier is within a predetermined range by comparing said digital signal to predetermined values, and for generating a control signal which increases the gain at said amplifier when said amplifier output is below a predetermined value and which decreases the gain at the amplifier when said amplifier output is above a predetermined value, to thereby maintain the level of the input signal to the A/D converter within a predetermined range.

5. The apparatus as set forth in claim 1 including a control means comprising a digital control device for automatically executing the operation of a pump for feeding specimens and washing solution into and out of the reaction cell under the control of a sequence program, wherein said digital control device periodically receives a timing signal which transfers the operational mode of the analyzing apparatus from the sequence program to a timing program, and wherein said timing program monitors and controls the time of operation of said pump by the sequence program.

6. The apparatus as set forth in claim 1 including control means for producing a control instruction to start a measurement sequence, said control means having a hold-free means for preventing operation of the analyzing apparatus from being advanced to a washing mode of operation after said chemical reaction has been completed, release means for releasing the condition of the analyzing apparatus from the hold-free condition, and decision means for determining which of the hold-free means and release means should be activated in response to the activation of a single manually actuable switch means on the basis of the present operational mode of the analyzing apparatus.

7. The apparatus as set forth in claim 1 further including means for storing data representing first and second conversion coefficient values obtained from two standard solutions having different blood sugar concentration values each in a different range corresponding to first and second ranges of reaction currents, respectively, means for determining which range of reaction current the measured reaction current from a blood test specimen falls within, and for calculating a blood sugar concentration value for the test specimen using the corresponding stored conversion coefficient value.

8. The apparatus as set forth in claim 7 further including means for calculating a third conversion coefficient value corresponding to a reaction current in a third range between the first and second ranges of reaction current values and for calculating a blood sugar concentration value for a test specimen using said third conversion coefficient when the reaction current is in said third range.

9. The apparatus as set forth in claim 1 further including means for lowering the value of the reaction current offset whenever the actual reaction current is less than the reaction current offset value, so that the actual reaction current value used to obtain the blood sugar concentration always exceeds the reaction current offset value.

10. A blood sugar analyzing apparatus having a reaction cell which houses a fixed enzyme membrane sensor and a measuring electrode and which receives a blood specimen which causes a chemical reaction between the blood specimen, said fixed enzyme membrane sensor measuring the blood sugar concentration in the blood specimen as a function of a reaction current signal generated in the sensor by the chemical reaction, said apparatus having means for monitoring the temperature in the reaction cell, means for comparing said monitored temperature value with a predetermined, measurement range to ascertain whether the temperature of the reaction cell is outside of said predetermined temperature range, and visual display means for indicating when said temperature is outside of said predetermined temperature range.

11. A blood sugar analyzing apparatus having a reaction cell which houses a fixed enzyme membrane sensor and a measuring electrode and which receives a blood specimen which causes a chemical reaction between the blood specimen, said fixed enzyme membrane sensor measuring the blood sugar concentration in the blood specimen on the basis of a reaction current signal generated in the sensor by the chemical reaction, said apparatus having means for monitoring the reaction current generated in the sensor, means for comparing the monitored value of reaction current with a predetermined reaction current measurement range to ascertain whether the reaction current is outside of said predetermined reaction current range, and visual display means for indicating when said reaction current is outside of said predetermined reaction current range.

12. A blood sugar analyzing apparatus having a reaction cell which houses a fixed enzyme membrane sensor and a measuring electrode and which receives a blood specimen which causes a chemical reaction between the blood specimen, said fixed enzyme membrane sensor measuring the blood sugar concentration in the blood specimen as a function of a reaction current signal generated in the sensor by the chemical reaction, said apparatus having means for monitoring the reaction current offset, means for comparing the reaction current offset with a predetermined reaction current offset measurement range to ascertain whether the reaction current offset is outside said predetermined reaction current offset range, and visual display means for indicating when said reaction current is outside of said predetermined range.

13. A blood sugar analyzing apparatus having a reaction cell which houses a fixed enzyme membrane sensor and a measuring electrode and which receives a blood specimen, said fixed enzyme membrane sensor measuring the blood sugar concentration in the blood specimen on the basis of a reaction current signal generated in the sensor by the chemical reaction, said apparatus having means for storing data representing first and second conversion coefficient values obtained from two standard solutions having different blood sugar concentration values each in a different range corresponding to first and second ranges of reaction currents, respectively, means for determining which range of reaction current the measured reaction current from a blood test specimen falls within, and for calculating a blood sugar concentration value for the test specimen using the corresponding stored conversion coefficient value.

14. The apparatus as set forth in claim 13 further including means for calculating a third conversion coefficient value corresponding to a reaction current in a third range between the first and second ranges of reaction current values and for calculating a blood sugar concentration value for a test specimen using said third conversion coefficient when the reaction current is in said third range.

15. The apparatus as set forth in claims 1, 10, 11, 12 or 13 wherein said display means comprises a printer.

* * * * *